(12) United States Patent
Shimizu et al.

(10) Patent No.: US 9,114,080 B2
(45) Date of Patent: Aug. 25, 2015

(54) CURABLE COMPOSITION FOR DENTISTRY

(75) Inventors: Tomonao Shimizu, Tokyo (JP); Tatsuya Yamazaki, Tokyo (JP); Hideki Kazama, Tokyo (JP); Hironobu Akizumi, Tokyo (JP)

(73) Assignee: TOKUYAMA DENTAL CORPORATION (JP)

( * ) Notice: Subject to any disclaimer, the term of this patent is extended or adjusted under 35 U.S.C. 154(b) by 60 days.

(21) Appl. No.: 14/000,085

(22) PCT Filed: Feb. 10, 2012

(86) PCT No.: PCT/JP2012/053085
§ 371 (c)(1),
(2), (4) Date: Aug. 16, 2013

(87) PCT Pub. No.: WO2012/111550
PCT Pub. Date: Aug. 23, 2012

(65) Prior Publication Data
US 2013/0324635 A1    Dec. 5, 2013

(30) Foreign Application Priority Data
Feb. 17, 2011  (JP) .................. 2011-032379

(51) Int. Cl.
| | | |
|---|---|---|
| B01F 3/04 | (2006.01) | |
| C08F 2/46 | (2006.01) | |
| B41J 2/16 | (2006.01) | |
| B29D 11/00 | (2006.01) | |
| C08G 61/04 | (2006.01) | |
| A61K 6/083 | (2006.01) | |
| C08G 83/00 | (2006.01) | |
| C08F 12/34 | (2006.01) | |

(52) U.S. Cl.
CPC ............. A61K 6/083 (2013.01); C08F 12/34 (2013.01); C08G 83/005 (2013.01); C08G 83/006 (2013.01)

(58) Field of Classification Search
CPC ... A61K 6/083; A61K 6/0017; C08G 83/005; C08G 83/006; C08F 12/34; C08L 101/005
USPC .......................... 522/173, 181, 1, 178; 520/1
See application file for complete search history.

(56) References Cited

U.S. PATENT DOCUMENTS 5,767,211 A      6/1998  Guan
7,659,324 B2 *   2/2010  Moszner et al. ............. 522/183

(Continued)

FOREIGN PATENT DOCUMENTS

| JP | 2001509179 A | 7/2001 |
|---|---|---|
| JP | 2006298919 | 11/2006 |
| JP | 2009149685 | 7/2009 |

(Continued)

OTHER PUBLICATIONS

Sato et al, Initiator-fragment incorporation radical polymerization of ethylene glycol dimethacrylate in the presence of 1,1-diphenylethylene: synthesis and charactierzation of soluble hyperbranched polymer nanoparticles, 7-33-2004, Polym Int, 53, 1503-1511.*

(Continued)

*Primary Examiner* — Ling Choi
*Assistant Examiner* — Jessica E Whiteley
(74) *Attorney, Agent, or Firm* — Cantor Colburn LLP

(57) ABSTRACT

A dental curable composition includes: a radically polymerizable monomer; a polymerization initiator; and a hyperbranched polymer, in which the hyperbranched polymer includes a unit structure represented by the general formula (I) and unit structures represented by the general formula (IIA) and/or the general formula (IIB) (in the general formula (I), A represents a single bond for bonding C and $R^1$, >C=O, —O—, or —COO—, $R^1$ represents a divalent saturated aliphatic hydrocarbon group or a divalent aromatic hydrocarbon group, and $R^2$ represents a hydrogen atom or a methyl group; and in the general formula (IIA) and the general formula (IIB), $R^3$, $R^4$, and $R^5$ each represent a hydrogen atom, an alkyl group, an alkoxycarbonyl group, an aryl group, or a cyano group, and $R^6$ represents an alkylene group).

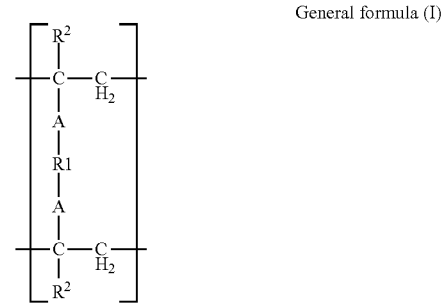

General formula (I)

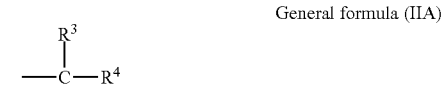

General formula (IIA)

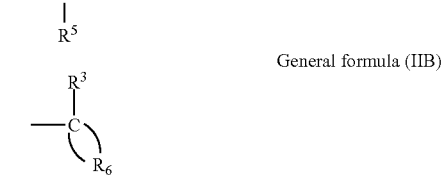

General formula (IIB)

5 Claims, No Drawings

(56) References Cited

U.S. PATENT DOCUMENTS

2008/0139692 A1     6/2008    Ishizu et al.
2012/0059136 A1     3/2012    Haraguchi et al.

FOREIGN PATENT DOCUMENTS

| | | |
|---|---|---|
| TW | 201107349 A | 3/2011 |
| WO | 9836729 A1 | 8/1998 |
| WO | 03013379 A2 | 2/2003 |
| WO | 2010126140 A1 | 11/2010 |

OTHER PUBLICATIONS

PCT International Search Report for PCT/JP2012/053085; International filing date: Feb. 10, 2012 with English Translation; Date of Mailing: Apr. 24, 2012; 2 pgs.

Extended European Search Report regarding Patent Application No. 12747182.9-1302/2676656 PCT/JP2012/053085; Date of Mailing: Sep. 8, 2014.

* cited by examiner

CURABLE COMPOSITION FOR DENTISTRY

CROSS REFERENCE TO RELATED APPLICATION

This is the U.S. national stage of application No. PCT/JP2012/053085, Filed on 10 Feb. 2012. Priority under 35 U.S.C. §365(b) is claimed from Japanese Application No. 2011032379, filed 17 Feb. 2011, the disclosure of which is also incorporated herein by reference.

TECHNICAL FIELD

The present invention relates to a dental curable composition.

BACKGROUND ART

A photocurable filling restoration material called a composite resin is generally widely used for restoration of a tooth damaged by caries from an aesthetic viewpoint. Such composite resin (dental curable composition) is a material containing a polymerizable monomer (monomer), a filling material (filler), and a photopolymerization initiator as main components and having further added thereto a pigment, an additive, and the like as necessary. In this case, a radically polymerizable monomer having radical polymerizability is generally used as the polymerizable monomer. Therefore, polymerization shrinkage inevitably occurs upon curing of the dental curable composition, that is, a polymerization reaction of the radically polymerizable monomer.

Hence, when the dental curable composition is filled into a cavity of a tooth that requires restoration and then subjected to polymerization curing, a gap is liable to be formed between the cured dental curable composition and an inner wall of the cavity. When such gap is formed, plaque is liable to be accumulated in the gap, and hence secondary caries is liable to develop. Further, the cured dental curable composition is liable to be detached out of the cavity. Accordingly, it is preferred that the polymerization shrinkage of the composite resin upon curing be as small as possible.

As a method of suppressing the polymerization shrinkage of the dental curable composition upon curing, there are given: a method involving using a radically polymerizable monomer having a high molecular weight; and a method involving using a cationically polymerizable monomer having a smaller polymerization shrinkage than that of the radically polymerizable monomer and subjecting the polymerizable monomer to polymerization curing through cationic ring-opening polymerization. Further, in addition to the foregoing, there are also proposals concerning methods involving using dendritic polymers having dendritically branched molecular chains, such as a hyperbranched polymer and dendrimer (see Patent Literatures 1 to 3).

The dendritic polymers are broadly divided into, for example, a hyperbranched polymer and dendrimer. A conventional polymer generally has a linear shape, while such dendritic polymer has actively introduced branches. Therefore, as compared to the conventional polymer having a linear shape, the dendritic polymer has, for example, the following features: 1) having a unique molecular structure; 2) having a size on a nanometer order; 3) being capable of forming a surface retaining a large number of functional groups; 4) being capable of being reduced in viscosity as compared to the linear polymer; 5) exhibiting a fine particle-like behavior because of less entanglement of molecules; and 6) having voids in the molecule. In this case, the hyperbranched polymer has an advantage in terms of its ease of synthesis as compared to the dendrimer, and thus is particularly advantageous in industrial production. In general, the dendrimer is synthesized by repeating protection and deprotection, while the hyperbranched polymer can be synthesized in one stage and can be synthesized simply.

For example, in Patent Literature 1, there is a proposal of a technology involving using a (meth)acryloyl terminated hyperbranched polyester having at least one ethylenically unsaturated moiety as a polymerizable resin for forming a dental material for the purpose of, for example, reducing a polymerization shrinkage of the dental material. Further, in Patent Literature 2, there is a proposal of a technology involving using a dendritic polymer as a polymerizable composition that may be utilized as a dental material and is low in shrinkage. For example, in Patent Literature 2, there is a disclosure of an example using a hyperbranched polyesteramide as a hyperbranched polymer. In addition, in Patent Literature 3, there is a proposal of a technology involving using, as a dental material, a dendritic compound in which a core, first shell, and second shell for forming a molecule are bonded via a polyurethane group and the second shell is modified by a reaction with a (meth)acrylate. According to the patent literature, undesired polymerization shrinkage is advantageously affected by this technology.

Further, in addition to Patent Literatures 1 to 3, there is a proposal of a technology involving using, as a crystal component for forming a dental material, one having a dendritic, hyperbranched, or star-shaped structure (Patent Literature 4). According to the patent literature, the crystal component to be used for the dental material preferably has a hydroxyl group at the end.

CITATION LIST

Patent Literature

[PTL 1] JP 2001-509179 W (e.g., claim 2 and Example 4)
[PTL 2] WO03/013379 (e.g., claim 1, Summary of the Invention, and Example 10)
[PTL 3] JP 2006-298919 A (e.g., claims 1 and 4, and paragraph 0017)
[PTL 4] JP 2009-149685 A (e.g., claims 15 and 41, paragraphs 0018 and 0059)

SUMMARY OF INVENTION

Technical Problem

In the case of using the dendritic polymer such as the hyperbranched polymer, the reason why a polymerization shrinkage ratio upon curing of the dental curable composition can be reduced is considered to be as described below. First, the dendritic polymer has a shape close to a spherical one unlike a general polymer having a linear shape. Therefore, when a polymer is dissolved in a solution, an increase in viscosity is small in the dendritic polymer as compared to the general polymer. Hence, when the dendritic polymer is used as a material for forming the dental curable composition, a large amount of the dendritic polymer can be added to the dental curable composition without significantly changing a filling ratio of the filler and handleability of the dental curable composition. That is, it is extremely easy to relatively increase a blending ratio of the dendritic polymer, and instead, relatively reduce a blending ratio of the monomer in components for forming the dental curable composition.

In addition to the foregoing, in the dendritic polymer, basically, there is almost no room for occurrence of large polymerization shrinkage due to polymerization unlike the monomer. Thus, when the blending ratio of the monomer contained in the dental curable composition can be reduced by using the dendritic polymer, the polymerization shrinkage ratio upon curing of the dental curable composition can be reduced.

However, in a dental curable composition using a conventional dendritic polymer exemplified in, for example, Patent Literatures 1 to 4, there are problems in that: (1) cured matter is colored through exposure of the cured matter to a food and beverage or the like in an oral environment after curing; and (2) cured matter is discolored through exposure of the cured matter to room light or natural light.

The present invention has been made in view of the above-mentioned circumstances, and an object of the present invention is to provide a dental composition that gives less colored and discolored cured matter as compared to a dental curable composition using a conventional dendritic polymer.

Solution to Problem

The above-mentioned object is achieved by the present invention described below. That is, a dental curable composition of the present invention is a dental curable composition, including: a radically polymerizable monomer; a polymerization initiator; and a hyperbranched polymer, in which the hyperbranched polymer includes a unit structure represented by the following general formula (I) and at least one unit structure selected from a unit structure represented by the following general formula (IIA) and a unit structure represented by the following general formula (IIB):

[Chem. 1]

General formula (I)

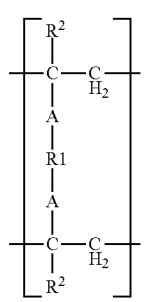

[Chem. 2]

General formula (IIA)

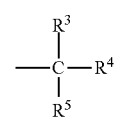

[Chem. 3]

General formula (IIB)

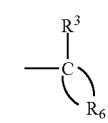

in the general formula (I), A represents a single bond for bonding C and $R^1$, >C=O, —O—, or —COO—, $R^1$ represents a divalent saturated aliphatic hydrocarbon group or a divalent aromatic hydrocarbon group, and $R^2$ represents a hydrogen atom or a methyl group;

in the general formula (IIA) and the general formula (IIB), $R^3$, $R^4$, and $R^5$ each represent a hydrogen atom, an alkyl group having 1 to 5 carbon atoms for forming a main chain, an alkoxycarbonyl group having 1 to 5 carbon atoms for forming a main chain, an aryl group, or a cyano group; and in the general formula (IIB), $R^6$ represents an alkylene group having 4 to 10 carbon atoms for forming a main chain.

A dental curable composition according to one embodiment of the present invention preferably further includes a filler.

In a dental curable composition according to another embodiment of the present invention, the hyperbranched polymer preferably has a molecular weight of 22,000 or more.

In a dental curable composition according to still another embodiment of the present invention, the polymerization initiator preferably includes a photopolymerization initiator.

In a dental curable composition according to still another embodiment of the present invention, the at least one unit structure selected from the unit structure represented by the general formula (IIA) and the unit structure represented by the general formula (IIB) preferably includes a unit structure represented by the following structural formula A.

[Chem. 4]

Structural formula A

Advantageous Effects of Invention

According to the present invention, it is possible to provide the dental composition that gives less colored and discolored cured matter as compared to a dental curable composition using a conventional dendritic polymer.

DESCRIPTION OF EMBODIMENTS

A dental curable composition according to this embodiment includes: a radically polymerizable monomer; a polymerization initiator; and a hyperbranched polymer, in which the hyperbranched polymer includes a unit structure represented by the following general formula (I) and at least one unit structure selected from a unit structure represented by the following general formula (IIA) and a unit structure represented by the following general formula (IIB).

[Chem. 5]

General formula (I)

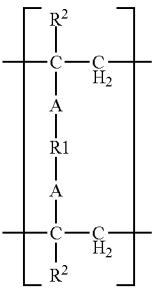

[Chem. 6]

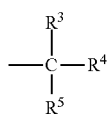

General formula (IIA)

[Chem. 7]

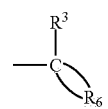

General formula (IIB)

In the general formula (I), A represents a single bond for bonding C and $R^1$ (that is, a state in which C and $R^1$ are simply bonded with a σ bond), >C=O, —O—, or —COO—, $R^1$ represents a divalent saturated aliphatic hydrocarbon group or a divalent aromatic hydrocarbon group, and $R^2$ represents a hydrogen atom or a methyl group.

In addition, in the general formula (IIA) and the general formula (IIB), $R^3$, $R^4$, and $R^5$ each represent a hydrogen atom, an alkyl group having 1 to 5 carbon atoms for forming a main chain, an alkoxycarbonyl group having 1 to 5 carbon atoms for forming a main chain, an aryl group, or a cyano group. Further, in the general formula (IIB), $R^6$ represents an alkylene group having 4 to 10 carbon atoms for forming a main chain.

It should be noted that the first unit structure represented by the general formula (I) and having four bonding sites is a unit structure for forming a multibranched structure of the hyperbranched polymer. In this case, to the four bonding sites, a first unit structure represented by the general formula (I) or a second unit structure selected from two kinds of unit structures represented by the general formula (IIA) and the general formula (IIB) can be bonded. Further, when the hyperbranched polymer contains another unit structure (third unit structure) except the general formula (I), the general formula (IIA), and the general formula (IIB), the third unit structure can also be bonded to the four bonding sites. In this case, the multibranched structure is formed by bonding the first unit structures together via at least any one of the four bonding sites. Further, the second unit structure as an end group that divides the multibranched structure can be bonded to up to three bonding sites out of the four bonding sites of the first unit structure. In this case, a content ratio (molar ratio) between the first unit structure and the second unit structure contained in the hyperbranched polymer is not particularly limited, but is controlled within preferably a range of 3:7 to 7:3, more preferably a range of 4:6 to 6:4. When the molar ratio is controlled within the range, a multibranched structure having appropriate branches can be formed and a remarkable increase in the viscosity of a solution obtained by dissolving the hyperbranched polymer in a solvent can be suppressed. It should be noted that, when the hyperbranched polymer also contains the third unit structure having two or more bonding sites, the content ratio (molar ratio) between the first unit structure and the second unit structure, which also depends on the content ratio of the third unit structure with respect to the first unit structure and the second unit structure, is, for example, selected from preferably a range of 1:9 to 7:3, more preferably a range of 2:8 to 7:3 in such a range that a multibranched structure can be formed. It should be noted that, also in this case, the content ratio (molar ratio) between the first unit structure and the second unit structure is controlled within still more preferably a range of 3:7 to 7:3, particularly preferably a range of 4:6 to 6:4.

It should be noted that the conventional dendritic polymer exemplified in, for example, Patent Literatures 1 to 4 contains large numbers of reactive unsaturated bonds, amino groups, and hydroxyl groups in the molecule, and these functional groups tend to be present in large numbers at the end. In addition, out of the reactive unsaturated bonds in those functional groups, one positioned at the end of the molecule may also be consumed by being utilized in a reaction with the radically polymerizable monomer contained in the dental curable composition in order to enhance the mechanical strength of cured matter, whereas one positioned in the molecule necessarily remains unreacted. Further, it is difficult to consume all the reactive unsaturated bonds present in large numbers at the end. Therefore, it is considered that, owing to the amino groups, the hydroxyl groups, or the unreacted reactive unsaturated bonds, cured matter obtained by curing a dental curable composition using the conventional dendritic polymer exemplified in, for example, Patent Literatures 1 to 4 is colored or discolored through reactions of these reactive functional groups when exposed to a food and beverage in the oral cavity or exposed to natural light or room light.

However, the hyperbranched polymer including a unit structure represented by the general formula (I) and at least one unit structure selected from a unit structure represented by the general formula (IIA) and a unit structure represented by the general formula (IIB) does not contain a reactive unsaturated bond and a reactive functional group such as an amino group or a hydroxyl group in its molecule. Further, the radically polymerizable monomer loses a reactive functional group through a polymerization reaction. Therefore, cured matter obtained by curing the dental curable composition according to this embodiment is hardly colored or discolored even when exposed to a food and beverage in an oral environment or exposed to natural light or room light.

Further, the conventional dendritic polymer exemplified in, for example, Patent Literatures 1 to 4 has a structure in which a branched molecular chain extends from the center side toward the outside. That is, at a portion closer to the end side of the branched molecular chain, the degree of freedom in movement of the molecular chain becomes higher. Therefore, the entanglement of adjacent branch moieties is liable to occur. Thus, an increase in viscosity is liable to occur in a dental curable composition using such dendritic polymer. The hyperbranched polymer including a unit structure represented by the general formula (I) and at least one unit structure selected from a unit structure represented by the general formula (IIA) and a unit structure represented by the general formula (IIB) has a net-like multibranched structure based on the unit structure represented by the general formula (I). That is, the movement of the branched molecular chain at both ends is very limited. Therefore, it is very difficult to entangle adjacent branch moieties, and thus an increase in the viscosity of a dental curable composition hardly occurs.

It should be noted that the hyperbranched polymer to be used in the dental curable composition according to this embodiment may contain, as the third unit structure, at least any one kind of unit structure selected from a unit structure represented by the following general formula (IIIA), a unit structure represented by the following general formula (IIIB), and a unit structure represented by the following general formula (IIIC). It should be noted that the third unit structure represented by the following general formula (IIIA) is contained as an impurity component in the hyperbranched polymer in synthesizing the hyperbranched polymer in some cases.

[Chem. 8]

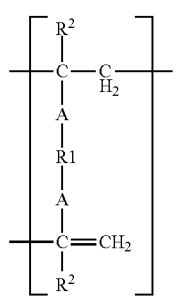

General formula (IIIA)

[Chem. 9]

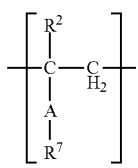

General formula (IIIB)

[Chem. 10]

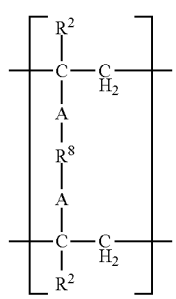

General formula (IIIc)

In this case, in the general formula (IIIA), the general formula (IIIB), and the general formula (IIIC), A, $R^1$, and $R^2$ are the same as A, $R^1$, and $R^2$ shown in the general formula (I). Further, in the general formula (IIIB), $R^7$ represents a monovalent saturated aliphatic hydrocarbon group or a monovalent aromatic hydrocarbon group, and in the general formula (IIIC), $R^8$ represents a tetravalent saturated aliphatic hydrocarbon group or a tetravalent aromatic hydrocarbon group.

It should be noted that the third unit structure represented by the general formula (IIIA) contains a reactive unsaturated bond, and hence is liable to promote the coloration or discoloration of cured matter. Therefore, when the hyperbranched polymer includes, in addition to the first unit structure represented by general formula (I) and the second unit structure selected from the unit structure represented by the general formula (IIA) and the unit structure represented by general formula (IIB), the third unit structure represented by the general formula (IIIA), the ratio of the third unit structure represented by the general formula (IIIA) in the whole unit structure is preferably 20 mol % or less, more preferably 10 mol % or less, still more preferably 5 mol % or less.

Further, a ratio between the third unit structure having two bonding sites as exemplified in the general formula (IIIA) and the general formula (IIIB) and the first unit structure represented by the general formula (I) falls within preferably a range of 6:4 to 0:10, more preferably a range of 4:6 to 0:10, and is most preferably 0:10. When the ratio between the third unit structure having two bonding sites and the first unit structure represented by the general formula (I) is controlled within the range, a multibranched structure having appropriate branches can be formed and an remarkable increase in the viscosity of a solution obtained by dissolving the hyperbranched polymer in a solvent can also be suppressed.

$R^1$ for forming the first unit structure represented by the general formula (I) and the third unit structure represented by the general formula (IIIA) represents a divalent saturated aliphatic hydrocarbon group or a divalent aromatic hydrocarbon group. In this case, the divalent saturated aliphatic hydrocarbon group may be any of a linear or cyclic one. Further, the number of carbon atoms is not particularly limited, but falls within preferably a range of 1 to 5, more preferably a range of 1 to 2. When the number of carbon atoms is controlled to 5 or less, the molecular chain moiety represented by $R^1$ is shortened, and hence the entanglement of the radically polymerizable monomer and hyperbranched polymer for forming the dental curable composition is suppressed. Thus, an increase in the viscosity of the dental curable composition in a paste form can be suppressed. Examples of the divalent linear saturated aliphatic hydrocarbon group include a methylene group, an ethylene group, a propylene group, and a butylene group. Further, examples of the divalent cyclic saturated aliphatic hydrocarbon group include a cyclopropylene group and a cyclobutylene group.

Further, the divalent aromatic hydrocarbon group may be any of a monocyclic one including one benzene ring, one containing two or more benzene rings and having a fused ring structure, and one containing two or more benzene rings and having no fused ring structure. The number of benzene rings contained in the divalent aromatic hydrocarbon group is not particularly limited, but falls within preferably a range of 1 to 2, in other words, it is particularly preferred that the divalent aromatic hydrocarbon group be a phenylene group. When the number of benzene rings is controlled to 2 or less, the entanglement of the radically polymerizable monomer and hyperbranched polymer for forming the dental curable composition is suppressed. Thus, an increase in the viscosity of the dental curable composition in a paste form can be suppressed. Examples of the divalent aromatic hydrocarbon group may include, in addition to the phenylene group, a naphthylene group and a biphenylene group.

It should be noted that, out of the groups represented by $R^1$ exemplified above, a phenylene group is particularly preferred. The phenylene group has less adverse influences on handleability in performing dental treatment using the dental curable composition in a paste form and the mechanical physical properties of cured matter even when the blending amount of the hyperbranched polymer to be added to the dental curable composition is changed to a large extent. Therefore, the composition design of the dental curable composition can be easily performed without bound to handleability and mechanical physical properties. Further, in the case of using the phenylene group as $R^1$, the mechanical strength of cured matter obtained by curing the dental curable composition can be improved.

Further, as each of $R^7$ for forming the third unit structure represented by the general formula (IIIB) and $R^8$ for forming the third unit structure represented by the general formula (IIIC), one having the same structure as that of $R^1$ except that there is a difference in valence may be utilized.

$R^3$, $R^4$, and $R^5$ for forming the second unit structures represented by the general formula (IIA) and the general formula (IIB) each represent a hydrogen atom, an alkyl group having 1 to 5 carbon atoms for forming a main chain, an alkoxycarbonyl groups having 1 to 5 carbon atoms for forming a main chain, an aryl group, or a cyano group. Of those, in particular, more preferred is an alkyl group having 1 to 5 carbon atoms for forming a main chain, an alkoxycarbonyl group having 1 to 5 carbon atoms for forming a main chain, or a cyano group. Examples of the alkyl group include a methyl group, an ethyl group, and a propyl group, examples of the alkoxycarbonyl group include a methoxycarbonyl group, an ethoxycarbonyl group, and a propoxycarbonyl group, and examples of the aryl group include a phenyl group. It should be noted that, as for the alkyl group and the alkoxycarbonyl group, when the number of carbon atoms for forming a main chain is controlled to 5 or less, in particular, when a methyl group or a methoxycarbonyl group is adopted, the main chain is shortened, and hence the entanglement of the radically polymerizable monomer and hyperbranched polymer for forming the dental curable composition is suppressed. Thus, an increase in the viscosity of the dental curable composition in a paste form can be suppressed.

Further, part of hydrogen atoms of the alkyl group, the alkoxycarbonyl group, and the aryl group may substituted by a substituent. The substituent is not particularly limited as long as it does not include a structure or group (a reactive unsaturated bond, an amino group, or a hydroxyl group) that causes coloration, and examples thereof may include an alkyl group having 1 to 3 carbon atoms such as a methyl group and an alkoxyl group having 1 to 3 carbon atoms such as a methoxy group. It should be noted that, as for the alkyl group and the alkoxyl group, when the number of carbon atoms is controlled to 3 or less, in particular, when a methyl group or a methoxy group is adopted, a main chain is shortened, and hence the entanglement of the radically polymerizable monomer and hyperbranched polymer for forming the dental curable composition is suppressed. Thus, an increase in the viscosity of the dental curable composition in a paste form can be suppressed.

$R^6$ for forming the second unit structure represented by the general formula (IIB) represents an alkylene group having 4 to 10 carbon atoms for forming a main chain. Examples of the alkylene group include a butylene group, a pentylene group, and a nonylene group. Further, part of hydrogen atoms of the alkylene group may be substituted by a substituent. The substituent is not particularly limited as long as it does not include a structure or group (a reactive unsaturated bond, an amino group, or a hydroxyl group) that causes coloration, and examples thereof may include an alkyl group having 1 to 3 carbon atoms such as a methyl group and an alkoxyl group having 1 to 3 carbon atoms such as a methoxy group. It should be noted that, when the number of carbon atoms for forming the main chain of the alkylene group is controlled to 4 or more, the strain of a ring formed of $R^6$ and carbon atoms to be bonded to both ends of $R^6$ can be suppressed. Therefore, such a risk that the ring becomes unstable owing to its strain to react with the surrounding substance, resulting in coloration can be suppressed. Further, when the number of carbon atoms for forming the main chain of the alkylene group is controlled to 10 or less, or when the number of carbon atoms of each of the alkyl group and the alkoxyl group to be selected as the substituent is controlled to 3 or less, in particular, when a methyl group or a methoxy group is adopted, the main chain is shortened, and hence the entanglement of the radically polymerizable monomer and hyperbranched polymer for forming the dental curable composition is suppressed. Thus, an increase in the viscosity of the dental curable composition in a paste form can be suppressed. It is particularly preferred that the alkylene group be a pentylene group from the viewpoint of achieving both of the suppression of a strain and the suppression of the increase in the viscosity.

It should be noted that the second unit structure represented by each of the general formula (IIA) and the general formula (IIB) is a structure derived from a raw material component (e.g., a monomer, a polymerization initiator, or an end group modifier) to be used in a synthesis process for the hyperbranched polymer to be used in the dental curable composition according to this embodiment. The raw material component is not particularly limited, and is exemplified by a known polymerization initiator, preferably an azo-based polymerization initiator disclosed in WO 2010/126140 A1. In this regard, however, in the dental curable composition according to this embodiment, out of the raw material component, polymerization initiator, or azo-based polymerization initiator listed above, there may be only adopted one that can have a structure represented by the general formula (IIA) and/or the general formula (IIB) after the completion of the synthesis of the hyperbranched polymer.

Specific examples of the second unit structure represented by the general formula (IIA) include the following structural formula A to structural formula K, and specific examples of the second unit structure represented by the general formula (IIB) include the following structural formula L and structural formula M. Such second unit structure represented by each of the structural formula A to the structural formula M is particularly suitable in terms of easy availability of the hyperbranched polymer.

[Chem. 11]

Structural formula A

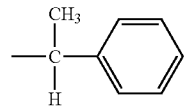

Structural formula B

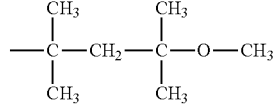

Structural formula C

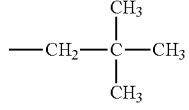

Structural formula D

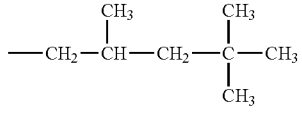

Structural formula E

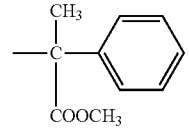

Structural formula F

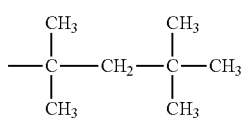

Structural formula G

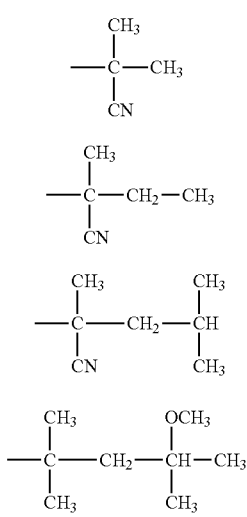

Examples of the hyperbranched polymer having the molecular structure described above include ones shown in the following items (1) to (5).

(1) Hyperbranched polymer disclosed in T. Hirano et al., J. Appl. Polym. Sci., 2006, 100, 664-670 (A: single bond for bonding C and $R^1$, $R^1$: phenylene group, $R^2$: hydrogen atom, $R^3$: —$CH_3$, $R^4$: —$CH_3$, $R^5$: —$COOCH_3$).

It should be noted that HYPERTECH (trade mark)/HA-DVB-500 (manufactured by NISSAN CHEMICAL INDUSTRIES. LTD., molecular weight determined by GPC method: 48,000, hydrodynamic mean diameter: 11.7 nm (in THF)) is given as a commercially available hyperbranched polymer having substantially the same molecular structure.

(2) Hyperbranched polymer disclosed in T. Hirano et al., Macromol. Chem. Phys., 205, 206, 860-868 (A: —COO—, $R^1$: —$(CH_2)_2$—, $R^2$: —$CH_3$, $R^3$: —$CH_3$, $R^4$: —$CH_3$, $R^5$: —$COOCH_3$)

It should be noted that, as a commercially available hyperbranched polymer having substantially the same molecular structure, there are given HYPERTECH (trade mark); HA-DMA-200 (molecular weight determined by GPC method: 22,000, hydrodynamic mean diameter: 5.2 nm (in THF)), HA-DMA-50 (trial sample, molecular weight determined by GPC method: 4,000), and HA-DMA-700 (trial sample, molecular weight determined by GPC method: 67,000), all of which are manufactured by NISSAN CHEMICAL INDUSTRIES. LTD.

(3) Hyperbranched polymer disclosed in T. Sato et al., Macromolecules, 2005, 38, 1627-1632 (A: —COO—, $R^1$: —$(CH_2)_4$—, $R^2$: —H, $R^3$: —$CH_3$, $R^4$: —$CH_3$, $R^5$: —$COOCH_3$).

(4) Hyperbranched polymer disclosed in T. Sato et al., Macromole. Mater. Eng., 2006, 291, 162-172.

It should be noted that this hyperbranched polymer includes the third unit structure represented by the general formula (IIIB). In this case, in the first unit structure represented by the general formula (I), A, $R^1$, and $R^2$ represent a single bond for bonding C and $R^1$, a phenylene group, and —H, respectively, and in the third unit structure represented by the general formula (IIIB), A, $R^7$, and $R^2$ represent —COO—, an ethyl group, and —H, respectively. In addition, in the second unit structure represented by the general formula (IIA), $R^3$, $R^4$, and $R^5$ represent —$CH_3$, —$CH_3$, and —$COOCH_3$, respectively.

(5) Hyperbranched polymer disclosed in T. Sato et al., Polym. Int. 2004, 53, 1138-1144.

It should be noted that this hyperbranched polymer includes the third unit structure represented by the general formula (IIIB). In this case, in the first unit structure represented by the general formula (I), A, $R^1$, and $R^2$ represent —COO—, —$(CH_2)_4$—, and —H, respectively and in the third unit structure represented by the general formula (IIIB), A, $R^7$, and $R^2$ represent —O—, a 2-methylpropyl group, and —H, respectively. In addition, in the second unit structure represented by the general formula (IIA), $R^3$, $R^4$, and $R^5$ represent —$CH_3$, —$CH_3$, and —CN, respectively.

The molecular weight of the hyperbranched polymer is not particularly limited, but is a mass average molecular weight of preferably 1,000 or more, more preferably 5,000 or more, still more preferably more than 25,000, which is measured by a gel permeation chromatography (GPC) method. When the mass average molecular weight is controlled to 1,000 or more, the hyperbranched polymer can easily have a spherical shape. Further, the upper limit of the molecular weight is not particularly limited. However, in the case where the molecular weight is too high, when the blending amount of the hyperbranched polymer is changed to a large extent, the handleability of the dental curable composition in a paste form is liable to be changed to a large extent in some cases. Therefore, the molecular weight is preferably 200,000 or less, more preferably 100,000 or less from a practical viewpoint. Further, when the molecular weight is controlled within the range, a spherical hyperbranched polymer having a hydrodynamic mean diameter in THF of about several nm to around 40 nm, which is measured by a dynamic light scattering method, can be obtained. It should be noted that the hydrodynamic mean diameter falls within preferably a range of several nm to 20 nm, more preferably a range of several nm to 15 nm. Further, the mass average molecular weight of the hyperbranched polymer is controlled to preferably 22,000 or more, more preferably 48,000 or more from the viewpoint of suppressing the solid-liquid separation of the dental curable composition in a paste form over a long period of time. It should be noted that, in this case, the upper limit value of the mass average molecular weight is preferably 200,000 or less from a practical viewpoint for the same reason as described above.

The refractive index of the hyperbranched polymer is not particularly limited, but is preferably close to the refractive index of the radically polymerizable monomer or a filling material from the viewpoint of imparting transparency to the dental curable composition. In this case, the refractive index of the radically polymerizable monomer or the filling material is generally about 1.4 to 1.7. Therefore, the refractive index of the hyperbranched polymer is also preferably about 1.4 to 1.7.

The blending amount of the hyperbranched polymer contained in the dental curable composition is not particularly limited, but is preferably 1 to 100 parts by mass, more preferably falls within a range of 5 to 40 parts by mass, with respect to 100 parts by mass of the radically polymerizable monomer. When the blending amount of the hyperbranched polymer is controlled to 1 part by mass or more, a polymerization shrinkage ratio upon curing the dental curable composition can be easily reduced more. Further, when the blending amount of the hyperbranched polymer is controlled to 40 parts by mass or less, the deterioration of handleability is prevented, and the mechanical strength of cured matter can be easily ensured by increasing the blending ratio of the filling material.

Next, materials for forming the dental curable composition except the hyperbranched polymer are described.

—Radically Polymerizable Monomer—

As the radically polymerizable monomer, a known one may be used without any particular limitation. As the radically polymerizable monomer to be generally suitably used, there are given, for example, ones shown in the following items (I) to (III).

(I) Bifunctional Radically Polymerizable Monomer
(i) Aromatic Compound-Based Bifunctional Radically Polymerizable Monomer 2,2-Bis(methacryloyloxyphenyl)propane, 2,2-bis[4-(3-methacryloyloxy)-2-hydroxypropoxyphenyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxytriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, and 2,2-bis(4-methacryloyloxyisopropoxyphenyl)propane, and acrylates corresponding to these methacrylates; diadducts each obtained by addition of a vinyl monomer having an —OH group, like a methacrylate such as 2-hydroxyethyl methacrylate, or 2-hydroxypropyl methacrylate, 3-chloro-2-hydroxypropyl methacrylate, or an acrylate corresponding to each of these methacrylates and a diisocyanate compound having an aromatic group, such as diisocyanatomethylbenzene or 4,4'-diphenylmethane diisocyanate; and the like.

(ii) Aliphatic Compound-Based Bifunctional Radically Polymerizable Monomer

Ethylene glycol dimethacrylate, diethylene glycol dimethacrylate, triethylene glycol dimethacrylate (hereinafter abbreviated as 3G), tetraethylene glycol dimethacrylate, neopentyl glycol dimethacrylate, 1,3-butanediol dimethacrylate, 1,4-butanediol dimethacrylate, 1,6-hexanediol dimethacrylate (hereinafter abbreviated as HD), 1,9-nonanediol dimethacrylate (hereinafter abbreviated as ND), and acrylates corresponding to these methacrylates; diadducts each obtained from an adduct of a vinyl monomer having an —OH group, like a methacrylate such as 2-hydroxyethyl methacrylate, 2-hydroxypropyl methacrylate, or 3-chloro-2-hydroxypropyl methacrylate, or an acrylate corresponding to each of these methacrylates and a diisocyanate compound, such as hexamethylene diisocyanate, trimethylhexamethylene diisocyanate, diisocyanatomethylcyclohexane, isophorone diisocyanate, or methylenebis(4-cyclohexyl isocyanate); 1,2-bis(3-methacryloyloxy-2-hydroxypropoxy)ethyl; and the like.

(II) Trifunctional Radically Polymerizable Monomer

Methacrylates, acrylates corresponding to the methacrylates, and the like, the metacrylates including trimethylolpropane trimethacrylate, trimethylolethane trimethacrylate, pentaerythritol trimethacrylate, and trimethylolmethane trimethacrylate.

(III) Tetraifunctional Radically Polymerizable Monomer

Pentaerythritol tetramethacrylate, pentaerythritol tetraacrylate, diadducts each obtained from an adduct of a diisocyanate compound and glycidol dimethacrylate, and the like, the diisocyanate compound being, for example, diisocyanatomethylbenzene, diisocyanatomethylcyclohexane, isophorone diisocyanate, hexamethylene diisocyanate, trimethylhexamethylene diisocyanate, methylenebis(4-cyclohexyl isocyanate), 4,4-diphenylmethane diisocyanate, or tolylene-2,4-diisocyanate.

A plurality of kinds of these polyfunctional (meth)acrylate-based radically polymerizable monomers may be used in combination as required.

Further, as required, there may be used monofunctional (meth)acrylate-based monomers including methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates, and radically polymerizable monomers other than the (meth)acrylate-based monomers.

—Polymerization Initiator—

As the polymerization initiator, a photopolymerization initiator, a chemical polymerization initiator, or a thermal polymerization initiator may be used, and two or more kinds of polymerization initiators may also be utilized in combination. It should be noted that, when the fact that the dental curable composition is generally used in the oral cavity is taken into consideration, it is preferred to use a photopolymerization initiator and/or a chemical polymerization initiator out of the three kinds of polymerization initiators. In addition, for reasons such as ease of handling and a small risk of entrapment of air bubbles into cured matter obtained by curing the dental curable composition, a photopolymerization initiator is most preferred. Hereinafter, the three kinds of polymerization initiators are described in more detail.

As the photopolymerization initiator, a known one to be used as a dental material may be used without any limitation. Typical examples of the photopolymerization initiator include photopolymerization initiators such as combinations of α-diketones and tertiary amines, combinations of acylphosphine oxides and tertiary amines, combinations of thioxanthones and tertiary amines, combinations of α-aminoacetophenones and tertiary amines, and combinations of aryl borates and photo acid generators.

The various compounds suitably used in the various photopolymerization initiators are exemplified below. Examples of the α-diketones include camphorquinone, benzil, α-naphthyl, acetonaphthene, naphthoquinone, p,p'-dimethoxybenzil, p,p'-dichlorobenzyl acetyl, 1,2-phenanthrenequinone, 1,4-phenanthrenequinone, 3,4-phenanthrenequinone, and 9,10-phenanthrenequinone.

Examples of the tertiary amines include N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, amyl p-dimethylaminobenzoate, methyl N,N-dimethylanthranilate, N,N-dihydroxyethylaniline, N,N- dihydroxyethyl-p-toluidine, p-dimethylaminophenethyl alcohol, p-dimethylaminostilbene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino) diethanol. One kind of those amines may be used alone, or two or more kinds thereof may be used as a blend.

Examples of the acylphosphine oxides include benzoyldiphenylphosphine oxide, 2,4,6-trimethylbenzoyldiphenylphosphine oxide, 2,6-dimethoxybenzoyldiphenylphosphine oxide, 2,6-dichlorobenzoyldiphenylphosphine oxide, and 2,3,5,6-tetramethylbenzoyldiphenylphosphine oxide.

Examples of the thioxanthones include 2-chlorothioxanthone and 2,4-diethylthioxanthone.

Examples of the α-aminoacetophenones include 2-benzyl-dimethylamino-1-(4-morpholinophenyl)-butanone-1, 2-benzyl-diethylamino-1-(4-morpholinophenyl)-butanone-1, 2-benzyl-dimethylamino-1-(4-morpholinophenyl)-propanone-1, 2-benzyl-diethylamino-1-(4-morpholinophenyl)-propanone-1, 2-benzyl-dimethylamino-1-(4-morpholinophenyl)-pentanone-1, and 2-benzyl-diethylamino-1-(4-morpholinophenyl)-pentanone-1.

One kind of the photopolymerization initiators may be used alone, or two or more kinds thereof may be used as a mixture.

The chemical polymerization initiator is a polymerization initiator that is formed of two or more components and generates a polymerization active species at around room temperature when all the components are mixed immediately before use. Such chemical polymerization initiator is typically an amine compound/organic peroxide-based one.

Specific examples of the amine compound include aromatic amine compounds such as N,N-dimethyl-p-toluidine, N,N-dimethylaniline, and N,N-diethanol-p-toluidine.

Typical examples of the organic peroxide include ketone peroxides, peroxyketals, hydroperoxides, dialkylperoxides, diacyl peroxides, peroxydicarbonates, peroxyesters, and diarylperoxides.

The organic peroxide is specifically exemplified below. Examples of the ketone peroxides include methyl ethyl ketone peroxide, cyclohexanone peroxide, methylcyclohexanone peroxide, methyl acetoacetate peroxide, and acetylacetone peroxide.

Examples of the peroxyketals include 1,1-bis(t-hexylperoxy)3,3,5-trimethylcyclohexane, 1,1-bis(t-hexylperoxy)cyclohexane, 1,1-bis(t-butylperoxy)3,3,5-trimethylcyclohexanone, 1,1-bis(t-butylperoxy)cyclohexane, 1,1-bis(t-butylperoxy)cyclodecane, 2,2-bis(t-butylperoxy)butane, n-butyl 4,4-bis(t-butyl peroxy)valerate, and 2,2-bis(4,4-di-t-butylperoxycyclohexyl)propane.

Examples of the hydroperoxides include P-methane hydroperoxide, diisopropylbenzene peroxide, 1,1,3,3-tetramethylbutyl hydroperoxide, cumene hydroperoxide, t-hexyl hydroperoxide, and t-butyl hydroperoxide.

Examples of the dialkyl peroxides include α,α-bis(t-butylperoxy)diisopropylbenzene, dicumyl peroxide, 2,5-dimethyl-2,5-bis(t-butylperoxy) hexane, t-butyl cumyl peroxide, di-t-butyl peroxide, and 2,5-dimethyl-2,5-bis(t-butylperoxy) hexane-3.

Examples of the diacyl peroxides include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, and benzoyl peroxides.

Examples of the peroxydicarbonates include di-n-propyl peroxydicarbonate, diisopropyl peroxydicarbonate, bis(4-t-butylcyclohexyl) peroxydicarbonate, di-2-ethoxyethyl peroxydicarbonate, di-2-ethylhexyl peroxydicarbonate, di-2-methoxybutyl peroxydicarbonate, and di(3-methyl-3-methoxybutyl)peroxydicarbonate.

Examples of the peroxyesters include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanonate, 2,5-dimethyl-2,5-bis(2-ethylhexanoylperoxy)hexane, 1-cyclohexyl-1-methylethyl peroxy-2-ethylhexanonate, t-hexyl peroxy-2-ethylhexanonate, t-butyl peroxy-2-ethylhexanonate, t-butyl peroxyisobutyrate, t-hexyl peroxyisopropylmonocarbonate, t-butyl peroxymaleic acid, t-butyl peroxy-3,5,5-trimethylhexanonate, t-butyl peroxylaurate, 2,5-dimethyl-2,5-bis(m-toluoylperoxy) hexane, t-butyl peroxyisopropylmonocarbonate, t-butyl peroxy-2-ethylhexylmonocarbonate, t-hexyl peroxybenzoate, 2,5-dimethyl-2,5bis(benzoylperoxy)hexane, t-butyl peroxyacetate, t-butyl peroxy-m-toluoylbenzoate, t-butyl peroxybenzoate, and bis(t-butyl peroxy)isophthalate.

In addition, for example, t-butyltrimethylsilyl peroxide or 3,3',4,4'-tetra(t-butylperoxycarbonyl)benzophenone may be used as the suitable organic peroxide.

The organic peroxide to be used has only to be appropriately selected and used. One kind of the organic peroxides may be used alone, or two or more kinds thereof may be used in combination. Of those, hydroperoxides, ketone peroxides, peroxyesters, and diacyl peroxides are particularly preferred from the viewpoint of a polymerization activity. In addition, of those, it is preferred to use an organic peroxide having a 10-hour half-life temperature of 60° C. or more from the viewpoint of storage stability of the dental curable composition.

A system in which a sulfinic acid such as benzenesulfinic acid or p-toluenesulfinic acid and a salt thereof is added to the initiator system formed of the organic peroxide and the amine compound, or a system in which a barbituric acid-based initiator such as 5-butylbarbituric acid is blended in the initiator system may also be used without any problem.

Further, an aryl borate compound/acidic compound-based polymerization initiator utilizing such a phenomenon that an aryl borate compound is decomposed by an acid to generate a radical may also be used.

The aryl borate compound is not particularly limited, and a known compound may be used as long as the compound has at least one boron-aryl bond in the molecule. Of those, it is preferred to use an aryl borate compound having 3 or 4 boron-aryl bonds in one molecule in consideration of storage stability, and it is more preferred to use an aryl borate compound having 4 boron-aryl bonds from the viewpoints of handling and easy synthesis and availability.

Examples of the aryl borate compound having 3 boron-aryl bonds in one molecule may include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, or butylquinolinium salts of a monoalkyltriphenylboron, a monoalkyltris(p-chlorophenyl)boron, a monoalkyltris(p- fluorophenyl) boron, a monoalkyltris(3,5-bistrifluoromethyl) phenylboron, a monoalkyltris[3,5-bis(1,1,1,3,3,3-hexafluoro-2-methoxy-2-propyl)phenyl]boron, a monoalkyltris(p-nitrophenyl)boron, a monoalkyltris(m-nitrophenyl)boron, a monoalkyltris(p-butylphenyl)boron, a monoalkyltris(m-butylphenyl)boron, a monoalkyltris(p-butyloxyphenyl)boron, a monoalkyltris(m-butyloxyphenyl)boron, a monoalkyltris(p-octyloxyphenyl)boron, and a monoalkyltris(m-octyloxyphenyl)boron (provided that the alkyl is anyone of n-butyl, n-octyl, and n-dodecyl in each of the compounds).

Examples of the aryl borate compound having 4 boron-aryl bonds in one molecule may include sodium salts, lithium salts, potassium salts, magnesium salts, tetrabutylammonium salts, tetramethylammonium salts, tetraethylammonium salts, tributylaminesalts, triethanolaminesalts, methylpyridiniumsalts, ethylpyridinium salts, butylpyridinium salts, methylquinolinium salts, ethylquinolinium salts, or butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl) boron, tetrakis(p-octyloxyphenyl)boron, and tetrakis(m-octyloxyphenyl)boron (provided that the alkyl is any one of n-butyl, n-octyl, or n-dodecyl in each of the compounds).

The various aryl borate compounds exemplified above may be used in combination of two kinds or more thereof.

The aryl borate compound/acidic compound-based polymerization initiator is also suitably used in combination with an organic peroxide and/or a transition metal compound. The organic peroxide is as described above. The transition metal compound is suitably a +IV-valent and/or +V-valent vanadium compound. Specific examples of the +IV-valent and/or +V-valent vanadium compound include divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) petoxide, sodium metavanadate(V), and ammonium metavanadate(V).

In addition, examples of the thermal polymerization initiator include: peroxides such as benzoyl peroxide, p-chlorobenzoyl peroxide, tert-butyl peroxy-2-ethylhexanoate, tert-butyl peroxydicarbonate, and diisopropyl peroxydicarbonate; azo compounds such as azobisisobutyronitrile; boron compounds such as tributylborane, tributylborane partial oxide, sodium tetraphenylborate, sodium tetrakis(p-fluorophenyl)borate, and triethanolamine tetraphenylborate; barbituric acids such as 5-butylbarbituric acid and 1-benzyl-5-phenylbarbituric acid; and sulfinates such as sodium benzenesulfinate and sodium p-toluenesulfinate.

—Filling Material—

It is particularly preferred to blend a filling material in the dental curable composition according to this embodiment. An effect of suppressing polymerization shrinkage upon polymerization can be increased more by blending a filling material in the dental curable composition according to this embodiment. Further, through use of the filling material, the handleability of the dental curable composition can be improved, or the mechanical physical properties of cured matter can be improved.

As the filling material, a known inorganic filling material or organic-inorganic composite filling material to be used as a filling material for a dental material is used without any limitation. Examples of the inorganic filling material include metal oxides such as quartz, silica, alumina, silica-titania, silica-zirconia, lanthanum glass, barium glass, and strontium glass. Further, as a cation releasing inorganic filling material, silicate glass, fluoroaluminosilicate glass, or the like may be used as necessary. One kind of the inorganic filling materials may be used alone, or two or more kinds thereof may be used as a mixture.

Further, as the organic-inorganic composite filling material, there may be utilized a particulate product obtained by adding a polymerizable monomer to the inorganic filling material exemplified above to prepare a paste, followed by polymerization, and pulverizing the resultant polymerization product.

The particle diameter of such filling material is not particularly not limited, and a filling material having an average particle diameter of 0.01 μm to 100 μm (particularly preferably 0.01 to 5 μm) to be generally used as a dental material may be appropriately used depending on purposes. Further, the refractive index of the filling material is also not particularly limited, a refractive index of a general dental inorganic filling material, i.e., a refractive index of from 1.4 to 1.7 may be used without limitation, and the refractive index has only to be appropriately set depending on purposes. A plurality of inorganic filling materials having different particle diameter ranges and refractive indices may be used in combination.

Further, from the viewpoint of improving the surface lubricating property of cured matter obtained by curing the dental curable composition, it is preferred to use a spherical inorganic filling material.

The inorganic filling material is preferably treated with a surface treatment agent typified by a silane coupling agent. In this case, the affinity between the inorganic filling material and the radically polymerizable monomer increases, and the mechanical strength and water resistance of cured matter can be improved. The surface treatment may be carried by a known method. In addition, as the silane coupling agent, there is suitably used methyltrimethoxysilane, methyltriethoxysilane, methyltrichlorosilane, dimethyldichlorosilane, trimethylchlorosilane, vinyltrichlorosilane, vinyltriethoxysilane, vinyltris(3-methoxyethoxy)silane, γ-methacryloyloxypropyltrimethoxysilane, γ-chloropropyltrimethoxysilane, γ-glycidoxypropyltrimethoxysilane, hexamethyldisilazane, or the like.

The blending amount of such filling material has only to be appropriately determined depending on use purposes in consideration of a viscosity upon mixing with the radically polymerizable monomer or the mechanical physical properties of cured matter, and generally falls within preferably a range of 50 to 1,500 parts by mass, more preferably a range of 70 to 1,000 parts by mass, with respect to 100 parts by mass of the radically polymerizable monomer.

—Other Addition Components—

Other components other than the radically polymerizable monomer, the photopolymerization initiator, the filling material, and the hyperbranched polymer may be further added to the dental curable composition according to this embodiment as necessary. For example, a coloring material such as a pigment, a fluorescent pigment, or a dye may be added in order to match the color tone of cured matter with the color tone of a tooth. Further, a UV absorbing agent may be added in order to prevent a cured body from being discolored by ultraviolet light. Further, a known additive such as a polymerization inhibitor, an antioxidant, an organic solvent, or a thickener may be used as necessary.

—Manufacturing Method for Dental Curable Composition—

A manufacturing method for the dental curable composition according to this embodiment is not particularly limited, and a known manufacturing method for a photopolymerizable composition may be utilized. In general, the dental curable composition according to this embodiment may be obtained by, under light shielding, weighing predetermined amounts of respective components to be blended and kneading the components until a homogeneous mixture is obtained.

EXAMPLES

Hereinafter, the present invention is described in more detail by way of Examples. However, the present invention is by no means limited to only Examples shown below.

(1) Abbreviated Names of Compounds used in Examples and Comparative Examples

The abbreviated names of compounds used in Examples and Comparative Examples are as described below.

(Radically Polymerizable Monomer)

Bis-GMA:
  2,2-Bis(4-(2-hydroxy-3-methacryloyloxypropoxy)phenyl)propane

D-2.6E:
  2,2-Bis(4-(methacryloyloxyethoxy)phenyl)propane

3G:
  Triethylene glycol dimethacrylate

UDMA:
  1,6-Bis(methacrylethyloxycarbonylamino)2,2,4-trimethylhexane

HD:
  1,6-Hexanediol dimethacrylate

ND:
  1,9-Nonanediol dimethacrylate (Polymerization Initiator)

($\alpha$-Diketone)

CQ:
  Camphorquinone (Amine Compound)

DMBE:
  Ethyl p-dimethylaminobenzoate (Filler)

10CF:
  Organic-inorganic composite filler (composite filler produced by using 25 parts by mass of a mixed organic component containing 36 mass % of bis-GMA, 24 mass % of 3G, and 40 mass % of HD and 75 parts by mass of spherical silica-zirconia (average particle diameter: 0.2 µm), average particle diameter: 10 µm)

20CF:
  Organic-inorganic composite filler (composite filler produced by using 25 parts by mass of bis-GMA and 75 parts by mass of spherical silica-zirconia (average particle diameter: 0.2 µm), average particle diameter: 20 µm)

30CF:
  Organic-inorganic composite filler (composite filler produced by using 25 parts by mass of a mixed organic component containing 36 mass % of bis-GMA, 24 mass % of 3G, and 40 mass % of HD and 75 parts by mass of spherical silica-zirconia (average particle diameter: 0.2 µm), average particle diameter: 30 µm)

0.15Si—Zr:
  Spherical silica-zirconia, γ-methacryloyloxypropyltrimethoxysilane surface treated product (average particle diameter: 0.15 µm)

0.3Si—Ti:
  Spherical silica-titania, γ-methacryloyloxypropyltrimethoxysilane surface treated product (average particle diameter: 0.3 µm)

0.45Si—Zr:
  Spherical silica-zirconia, γ-methacryloyloxypropyltrimethoxysilane surface treated product (average particle diameter: 0.45 µm)

(Hyperbranched Polymer)

HA-DMA-200:
  NISSAN CHEMICAL INDUSTRIES, LTD., molecular weight determined by GPC method: 22,000, hydrodynamic mean diameter: 5.2 nm (in THF)

HA-DVB-500:
  NISSAN CHEMICAL INDUSTRIES, LTD., molecular weight determined by GPC method: 48,000, hydrodynamic mean diameter: 11.7 nm (in THF)

HA-DMA-50:
  NISSAN CHEMICAL INDUSTRIES, LTD., molecular weight determined by GPC method: 4,000

HA-DMA-700:
  NISSAN CHEMICAL INDUSTRIES, LTD., molecular weight determined by GPC method: 67,000

HPS-200:
  NISSAN CHEMICAL INDUSTRIES, LTD., molecular weight determined by GPC method: 23,000, hydrodynamic mean diameter: 7.5 nm (in THF)

PEI:
  Poly(ethylenimide), manufactured by Polysciences, molecular weight: 10,000

DVA-IBVE
  Hyperbranched polymer synthesized under the conditions shown in Run16 in Table 1 in T. Sato et al., Polym. Int. 2004, 53, 1138-1144

It should be noted that HPS-200 is a hyperbranched polymer having a molecular structure represented by the following structural formula 1. In this case, in the structural formula 1, n represents an integer of 1 or more.

[Chem. 14]

Structural formula 1

(2) Composition of Dental Curable Composition

Table 1 to Table 3 show the composition of a dental curable composition according to each of Examples and Comparative Examples.

TABLE 1

|  |  | Example A1 | Example A2 | Example A3 | Comparative Example A1 | Comparative Example A2 | Comparative Example A3 |
|---|---|---|---|---|---|---|---|
| Matrix composition (parts by mass) | Matrix composition A | 26 | 26 | 26 | 29 | 26 | 26 |
| Hyperbranched polymer (parts by mass) | HA-DMA-200 | 3 | — | — | — | — | — |
|  | HA-DVB-500 | — | 3 | — | — | — | — |
|  | DVA-IBVE | — | — | 3 | — | — | — |
|  | HPS-200 | — | — | — | — | 3 | — |
|  | PEI | — | — | — | — | — | 3 |
| Filler composition (parts by mass) | Filler composition A | 71 | 71 | 71 | 71 | 71 | 71 |

TABLE 2

|  |  | Example B1 | Example B2 | Example B3 | Example B4 | Example B5 | Comparative Example B1 | Comparative Example B2 | Comparative Example B3 |
|---|---|---|---|---|---|---|---|---|---|
| Matrix composition (parts by mass) | Matrix composition B | 18 | 18 | 18 | 18 | 18 | 22 | 18 | 18 |
| Hyperbranched polymer (parts by mass) | HA-DMA-200 | 4 | — | — | — | — | — | — | — |
|  | HA-DVB-500 | — | 4 | — | — | — | — | — | — |
|  | HA-DMA-50 | — | — | 4 | — | — | — | — | — |
|  | HA-DMA-700 | — | — | — | 4 | — | — | — | — |
|  | DVA-IBVE | — | — | — | — | 4 | — | — | — |
|  | HPS-200 | — | — | — | — | — | — | 4 | — |
|  | PEI | — | — | — | — | — | — | — | 4 |
| Filler composition (parts by mass) | Filler composition B | 78 | 78 | 78 | 78 | 78 | 78 | 78 | 78 |

TABLE 3

|  |  | Example C1 | Example C2 | Example C3 | Comparative Example C1 | Comparative Example C2 | Comparative Example C3 |
|---|---|---|---|---|---|---|---|
| Matrix composition (parts by mass) | Matrix composition C | 18 | 18 | 18 | 20 | 18 | 18 |
| Hyperbranched polymer (parts by mass) | HA-DMA-200 | 2 | — | — | — | — | — |
|  | HA-DVB-500 | — | 2 | — | — | — | — |
|  | DVA-IBVE | — | — | 2 | — | — | — |
|  | HPS-200 | — | — | — | — | 2 | — |
|  | PEI | — | — | — | — | — | 2 |
| Filler composition (parts by mass) | Filler composition C | 80 | 80 | 80 | 80 | 80 | 80 |

It should be noted that the matrix composition A, matrix composition B, matrix composition C, filler composition A, filler composition B, and filler composition C shown in Table 1 to Table 3 are compositions shown below.

(Matrix Composition A)
D-2.6E: 70 parts by mass
3G: 20 parts by mass
UDMA: 10 parts by mass
CQ: 0.2 part by mass
DMBE: 0.35 part by mass
  (Matrix Composition B)
bis-GMA: 60 parts by mass
3G: 40 parts by mass
CQ: 0.2 part by mass
DMBE: 0.28 part by mass
  (Matrix Composition C)
D-2.6E: 60 parts by mass
ND: 20 parts by mass
UDMA: 20 parts by mass
CQ: 0.2 part by mass
DMBE: 0.35 part by mass
  (Filler Composition A)
0.45Si—Zr: 70 parts by mass
0.3Si—Ti: 30 parts by mass
  (Filler Composition B)
20CF: 60 parts by mass
0.15Si—Zr: 40 parts by mass
  (Filler Composition C)
30CF: 36 parts by mass
10CF: 24 parts by mass
0.15Si—Zr: 40 parts by mass
  (Evaluation Results)

The dental curable composition according to each of Examples and Comparative Examples was measured for its polymerization shrinkage ratio and evaluated by a coloration resistance test and a light resistance test. Further, each of Examples B1 to B4 and Comparative Examples B1 to B3 was evaluated for its number of days before solid-liquid separation, and each of Examples A1 and A2 was evaluated for its Flexural strength. Table 4 to Table 7 show the results.

TABLE 4

|  | Polymerization shrinkage ratio (%) | Coloration resistance test | Light resistance test |
|---|---|---|---|
| Example A1 | 1.9 | A | B |
| Example A2 | 2.0 | A | B |
| Example A3 | 2.0 | A | B |
| Comparative Example A1 | 2.5 | A | B |
| Comparative Example A2 | 2.1 | C | C |
| Comparative Example A3 | 1.9 | C | B |

TABLE 5

|  | Polymerization shrinkage ratio (%) | Coloration resistance test | Light resistance test | Number of days before solid-liquid separation (days) |
|---|---|---|---|---|
| Example B1 | 1.1 | A | B | 35 |
| Example B2 | 1.2 | A | B | 38 |
| Example B3 | 1.1 | A | B | 33 |
| Example B4 | 1.1 | A | B | 37 |
| Example B5 | 1.1 | A | B | Unevaluated |
| Comparative Example B1 | 1.4 | A | B | 14 |
| Comparative Example B2 | 1.2 | C | C | 23 |
| Comparative Example B3 | 1.1 | C | B | Unable to be evaluated |

TABLE 6

|  | Polymerization shrinkage ratio (%) | Coloration resistance test | Light resistance test |
|---|---|---|---|
| Example C1 | 1.0 | A | B |
| Example C2 | 1.0 | A | B |
| Example C3 | 1.0 | A | B |
| Comparative Example C1 | 1.2 | A | B |
| Comparative Example C2 | 1.0 | C | C |
| Comparative Example C3 | 1.0 | C | B |

TABLE 7

|  | Flexural strength [MPa] |
|---|---|
| Example A1 | 96 |
| Example A2 | 148 |

When the evaluation results were compared among Examples and Comparative Examples using substantially the same amounts of the same matrix composition and the same filler composition, the following facts were found. First, each of Examples A1 to A3 (or Examples B1 to B5 or Examples C1 to C3) using a hyperbranched polymer had a small polymerization shrinkage ratio as compared to Comparative Example A1 (or Comparative Example B1 or Comparative Example C1) using no hyperbranched polymer. Further, each of Examples A1 to A3 (or Examples B1 to B5 or Examples C1 to C3) using HA-DMA-200, HA-DVB-500, HA-DMA-50, HA-DMA-700, or DVA-IBVE as a hyperbranched polymer gave comparable results in both of the coloration resistance test and the light resistance test as compared to a composite resin using no hyperbranched polymer (Comparative Example A1, Comparative Example B1, or Comparative Example C1).

On the other hand, Comparative Example A2 (or Comparative Example B2 or Comparative Example C2) using a hyperbranched polymer HPS-200, which had a double bond at the end and had an amino group, gave poor results in both of the coloration resistance test and the light resistance test as compared to Comparative Example A1 (or Comparative Example B1 or Comparative Example C1) using no hyperbranched polymer. Further, Comparative Example A3 (or Comparative Example B3 or Comparative Example C3) using a polyethylenimine having an amino group as a hyperbranched polymer showed a comparable color tone change in the light resistance test but was remarkably colored in the coloration resistance test as compared to Comparative Example A1 (or Comparative Example B1 or Comparative Example C1) using no hyperbranched polymer. From the results, it is estimated that the coloration resistance of cured matter is deteriorated in the case of using a hyperbranched polymer having an amino group with high hydrophilicity, and the light resistance of cured matter is deteriorated in the case of using a hyperbranched polymer having a double bond with high reactivity at the end.

Each of Examples B1 to B4 using HA-DMA-200, HA-DVB-500, HA-DMA-50, and HA-DMA-700, respectively, as hyperbranched polymers was able to be stored for 4 weeks or more without the occurrence of solid-liquid separation. In addition, the comparison of Examples B1, B3, and B4 using hyperbranched polymers that had the same molecular structure and were different only in molecular weight revealed that a hyperbranched polymer having a higher molecular weight was able to suppress solid-liquid separation over a longer period of time. On the other hand, each of Comparative Examples B1 and B2 underwent solid-liquid separation in 2 to 3 weeks. Further, Comparative Example B3 was unable to be evaluated because the dental curable composition was cured in several days after the start of the test.

Further, the results shown in Table 7 revealed that Example A2 using HA-DVB-500, which had a phenylene group as $R^1$, gave a more excellent Flexural strength than that of Example A1.

It should be noted that a measurement method for a polymerization shrinkage ratio, test methods and evaluation criteria for a coloration resistance test and a light resistance test, an evaluation method for the number of days before solid-liquid separation, and a measurement method for a Flexural strength, the polymerization shrinkage ratio, the coloration resistance test and light resistance test, the number of days before solid-liquid separation, and the Flexural strength being shown in Table 4 to Table 6, are as described below.

—Polymerization Shrinkage Ratio—

A plunger made of SUS with a diameter of 3 mm and a height of 4 mm was inserted into a split mold made of SUS having a pore with a diameter of 3 mm and a height of 7 mm so as to adjust the height of the pore to 3 mm. Next, a dental curable composition was filled into the pore, and then a polypropylene film was pressure-bonded to the upper end of the pore. After that, the resultant was mounted onto a stage made of glass equipped with a dental irradiation device (TOKUSO POWER LITE, manufactured by Tokuyama Dental Corporation; optical output density: 700 mW/cm$^2$) in a state in which a surface of the split mold made of SUS to which the polypropylene film was attached faced downward.

Then, a short needle capable of measuring a minute needle motion was further brought into contact from above the plunger made of SUS. In this state, the dental curable composition was subjected to polymerization curing with the dental irradiation device, and a shrinkage ratio [%] of 3 minutes after the start of irradiation was calculated from a movement distance of the probe in a vertical direction.

—Coloration Resistance Test—

A dental curable composition was filled into a mold made of a polyacetal having a thickness of 3 mm and having a through-hole with a diameter of 8 mm. After that, a polypropylene film was pressure-bonded to each of both ends of the through-hole. Next, through use of a dental photoirradiation device (TOKUSO POWER LITE, manufactured by Tokuyama Dental Corporation; optical output density: 700 mW/cm$^2$), the resultant was irradiated with light for 10 seconds to produce a cured body (test piece). The resultant test piece was buffed for its surface. After that, the test piece whose surface had been buffed was immersed in 100 ml of a coffee aqueous solution having a concentration of 7.4 mass % at 80° C. for 24 hours. After the immersion, the test piece was washed with water, dried, and visually observed for its degree of coloration. At this time, the degrees of coloration of samples produced by using the same matrix composition and the same filler composition were relatively evaluated by using a dental curable composition containing no hyperbranched polymer as a reference sample. Criteria for the evaluation are as described below.

A: The degree of coloration of the evaluated sample is substantially the same as the degree of coloration of the reference sample.
B: The degree of coloration of the evaluated sample is slightly poor as compared to the degree of coloration of the reference sample.
C: The degree of coloration of the evaluated sample is remarkably poor as compared to the degree of coloration of the reference sample.

—Light Resistance Test—

A dental curable composition was filled into a mold made of a polyacetal having a thickness of 1 mm and having a through-hole with a diameter of 15 mm. After that, a polypropylene film was pressure-bonded to each of both ends of the through-hole. Next, through use of a dental photoirradiation device (TOKUSO POWER LITE, manufactured by Tokuyama Dental Corporation; optical output density: 700 mW/cm$^2$), five sites in the circle of the dental curable composition having a circle shape filled into the through-hole (the central portion of the circle and positions at intervals of 90° in the circumferential direction in the vicinity of the circumference) were irradiated with light for 10 seconds per site so that the entire composition was irradiated with light. Thus, a cured body (test piece) having a disc shape was obtained. Next, half of the resultant test piece was covered with an aluminum foil, and exposure to simulated sunlight with a xenon weather meter (manufactured by Suga Test Instruments Co., Ltd., light intensity: 40 W/m$^2$) was performed for 4 hours in total. After that, each of a portion covered with the aluminum foil (unexposed portion) and a portion exposed to simulated sunlight (exposed portion) was visually observed for its color tone. Evaluation criteria therefor are as described below.

A: The color tone of the unexposed portion is substantially the same as the color tone of the exposed portion.
B: The color tone of the unexposed portion slightly differs from the color tone of the exposed portion.
C: The color tone of the unexposed portion remarkably differs from the color tone of the exposed portion.

—Number of Days Before Solid-Liquid Separation—

A dental curable composition in a paste form was filled into a syringe (manufactured by Tokuyama Dental Corporation: syringe for PALFIQUE ESTELITE ZQUICK) and stored at 50° C. After the start of the storage, the syringe was taken out every day, a cap was opened to visually observe a surface of the paste, and the presence or absence of separation between a solid component and a liquid component was confirmed.

—Flexural Strength—

The measurement of a Flexural strength was performed according to the following procedure. First, a dental curable composition was filled into a mold form made of stainless steel, and a polypropylene film was pressure-bonded to each of both surfaces of the dental curable composition exposed at openings on front and back surfaces of the mold form made of stainless steel. In this state, through use of a dental photoirradiation device (TOKUSO POWER LITE, manufactured by Tokuyama Dental Corporation; optical output density: 700 mW/cm$^2$), photoirradiation was performed from each of the front and back surface sides. The photoirradiation was carried out for 10 seconds per time for one surface, and carried out a total of five times by changing an irradiation position so that the entire dental curable composition was irradiated with light. Further, the photoirradiation was performed by bringing the dental photoirradiation device into close contact with the polypropylene film. Thus, a cured body was obtained. Next, the cured body was stored in water at 37° C. overnight, and then further abraded with #1500 waterproof abrasive paper to afford a test piece having a rectangular column shape (2 mm×2 mm×25 mm). After that, the sample piece was mounted onto a tester (manufactured by Shimadzu Corporation, Autograph AG5000D), and measured for its three-point bending fracture strength at a distance between supporting points of 20 mm and a cross-head speed of 1 mm/min. Then, an average of values obtained by the measurement of five test pieces was defined as a Flexural strength.

The invention claimed is:

1. A dental curable composition, comprising:
   a radically polymerizable monomer;
   a polymerization initiator; and
   a hyperbranched polymer,
   wherein the hyperbranched polymer consists essentially of a unit structure represented by the following general formula (I), at least one unit structure selected from a unit structure represented by the following general formula (IIA), a unit structure represented by the following general formula (IIB), and a unit structure represented by the following general formula (IIIA) and
   wherein the ratio of the unit structure represented by the general formula (IIIA) in a whole unit structure is 5 mol % or less:

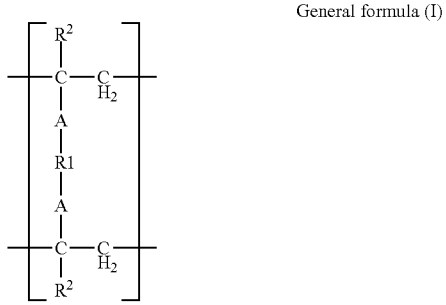

General formula (I)

-continued

General formula (IIA)

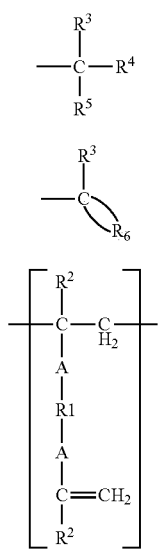

General formula (IIB)

General formula (IIIA)

in the general formula (I), A represents a single bond for bonding C and $R^1$, $>C=O$, —O—, or —COO—, $R^1$ represents a divalent saturated aliphatic hydrocarbon group or a divalent aromatic hydrocarbon group, and $R^2$ represents a hydrogen atom or a methyl group;

in the general formula (IIA) and the general formula (IIB), $R^3$, $R^4$, and $R^5$ each represent a hydrogen atom, an alkyl group having 1 to 5 carbon atoms for forming a main chain, an alkoxycarbonyl group having 1 to 5 carbon atoms for forming a main chain, an aryl group, or a cyano group; and in the general formula (IIB), $R^6$ represents an alkylene group having 4 to 10 carbon atoms for forming a main chain; and in the general formula (IIIA), A, $R^1$, and $R^2$ are the same as A, $R^1$, and $R^2$ shown in the general formula (I).

2. A dental curable composition according to claim 1, further comprising a filler.

3. A dental curable composition according to claim 1, wherein the hyperbranched polymer has a molecular weight of 22,000 or more.

4. A dental curable composition according to claim 1, wherein the polymerization initiator comprises a photopolymerization initiator.

5. A dental curable composition according to claim 1, wherein the at least one unit structure selected from the unit structure represented by the general formula (IIA) and the unit structure represented by the general formula (IIB) comprises a unit structure represented by the following structural formula A.

Structural formula A

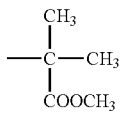

* * * * *